United States Patent [19]

Lachhein et al.

[11] Patent Number: 4,960,887
[45] Date of Patent: Oct. 2, 1990

[54] PROCESS FOR THE PREPARATION OF PYRIMIDINES

[75] Inventors: Stephen Lachhein, Hofheim am Taunus; Hans-Joachim Ressel, Hattersheim am Main, both of Fed. Rep. of Germany

[73] Assignee: Hoechst Aktiengesellschaft, Frankfurt am Main, Fed. Rep. of Germany

[21] Appl. No.: 156,182

[22] Filed: Feb. 16, 1988

[30] Foreign Application Priority Data

Feb. 18, 1987 [DE] Fed. Rep. of Germany ....... 3705084

[51] Int. Cl.$^5$ .................. C07D 239/42; C07D 239/52; C07D 239/58
[52] U.S. Cl. ..................................... 544/320; 544/321
[58] Field of Search ....................... 544/320, 322, 321; 548/152, 161

[56] References Cited

U.S. PATENT DOCUMENTS 4,169,719 10/1979 Levitt ........................................ 71/92
4,492,598 1/1985 Willms et al. ............................ 71/93

FOREIGN PATENT DOCUMENTS 61-134378 6/1986 Japan .
1256834 12/1971 United Kingdom ................ 548/161

OTHER PUBLICATIONS

J. Am. Chem. Soc., "Orthoesters and Related Compounds from Mslono-and Succinonitriles", S. M. McElvain and Juel. P. Schroeder, vol. 71, p. 40 (1949).

Primary Examiner—John M. Ford
Attorney, Agent, or Firm—Curtis, Morris & Safford

[57] ABSTRACT

The invention relates to a process for the preparation of compounds of the formula I

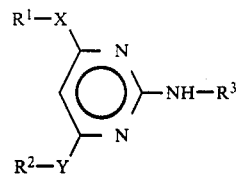

in which X and Y denote O or S; $R^1$ and $R^2$ denote (substituted) alkyl, $R^3$ denotes H or a —$COR^4$ radical in which $R^4$ is alkyl, halogenoalkyl, alkoxy, halogenoalkoxy, (substituted) phenyl or (substituted) phenoxy, wherein a propanediimidate of the formula II

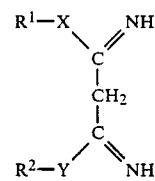

or a salt thereof is reacted, in an inert solvent and in the presence of a base, with a carbonic acid imine derivative of the formula III

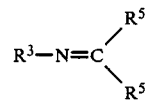

in which $R^5$ denotes halogen, alkoxy, alkylthio, phenoxy or phenylthio.

10 Claims, No Drawings

PROCESS FOR THE PREPARATION OF PYRIMIDINES

The invention relates to a process for the preparation of pyrimidines of the formula I

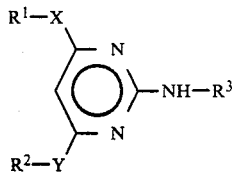

in which
X and Y independently of one another denote oxygen or sulfur and
$R^1$ and $R^2$ independently of one another denote $(C_1-C_4)$-alkyl, $(C_1-C_4)$alkoxy-$(C_1-C_2)$alkyl or halogeno$(C_1-C_4)$alkyl and
$R^3$ denotes H or a radical $-COR^4$ in which $R^4$ denotes
$(C_1-C_4)$alkyl, halogeno-$(C_1-C_4)$alkyl, $(C_1-C_4)$ halogeno-$(C_{1-C4})$alkoxy, phenyl or phenoxy the latter both of which are unsubstituted or monosubstituted to trisubstituted substituted by halogen, $(C_1-C_4)$alkoxy or $(C_1-C_4)$ alkyl,
which comprises reacting a propanediimidate of the formula II

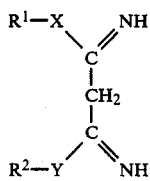

in which $R^1$ and $R^2$ are as defined in formula I, or one of its salts, in an inert solvent and in the presence of a base, with a carbonic acid imine derivative of the formula III

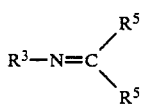

in which
$R^3$ is as defined in formula I and
the $R^5$s independently of one another denote halogen, $(C_1-C_4)$alkoxy, $(C_1-C_4)$alkylthio, phenoxy or phenylthio.

Compounds of the formula I are valuable intermediates in the preparation of sulfonylureas having a herbicidal action (U.S. Pat. No. 4,169,719 and EP-A No. 071 958 (U.S. patent application No. 4 492 598)).

A process is known for the preparation of the compounds I in the case where $R^3 = H$, in which these compounds are prepared in a two-stage or three-stage process by reacting propanediimidates with an aqueous cyanamide solution or with cyanogen chloride (EP-A No. 0 024 200). The formation and subsequent isolation of an N-cyanoimidate as an intermediate are characteristic process features of this process.

A process for the preparation of pyrimidines having alkoxycarbonylamino radicals, in which propanediimidates are reacted with an alkoxycarbonyl isothiocyanate is also described in JP-A No. 61/34,378.

Surprisingly, the process according to the invention takes place as a single-stage process involving simple process technology and without intermediates which can be isolated, and affords the compounds I directly and in a high yield. By-products are formed only to a minor extent. After the completion of the reaction and the subsequent filtration, the end product is left in a state of high purity.

The process according to the invention is advantageously carried out by isolating the propanediimidate of the formula II or the mono-salt or di-salt thereof and reacting it in solution or as a suspension with a compound of the formula III at reaction temperatures from $-20°$ to $100°$ C., preferably $-20°$ to $60°$ C., in the presence of a base.

Salts of the propanediimidate which are preferably employed are those of hydrofluoric, hydrochloric or hydrobromic acid or of sulfuric or phosphoric acid. Examples of halogenoalkyl radicals for $R^1$, $R^2$ and $R^3$ are $CH_2Cl$, $CHC_2$, $CCl_3$, $CH_2CH_2Cl$ or $CH_2CF_3$. The preferred meaning of X and Y is oxygen, of $R^1$ and $R^2$ is $(C_1-C_4)$alkyl, in particular methyl, of $R^3$ a hydrogen atom or a $-COR^4$ radical in which $R^{14}$ denotes $(C_1-C_4)$alkyl or $(C_1-C_4)$-alkoxy, alkoxy, especially $(C_1-C_4)$alkyl, and of each of the $R^{15}$s $(C_1-C_4)$alkoxy, $(C_1-C_4)$alkylthio or especially chlorine, $R^3$ preferably not being a hydrogen atom in the event that each of the $R^5$s is a chlorine atom.

Suitable inert solvents are those which are inert under the particular reaction conditions. Examples of solvents which can be used are water, aliphatic alcohols having 1 to 4 carbon atoms, such as methanol and ethanol, aliphatic ketones, such as acetone and methyl isobutyl ketone, halogenated aliphatic hydrocarbons having 1 to 3 carbon atoms, such as methylene chloride and chloroform, aliphatic and cycloaliphatic ethers, such as diethyl ether, dioxane and tetrahydrofuran, aliphatic esters having 3 to 6 carbon atoms, such as methyl acetate, ethyl acetate and butyl acetate, aromatic and cycloaliphatic hydrocarbons having 5 or 6 ring atoms, such as toluene, xylene, hexane and cyclohexane, aliphatic nitriles, such as acetonitrile, or mixtures thereof.

Bases which can be employed are the compounds of the formula II itself or inorganic bases, such as alkali or alkaline earth metal hydroxides, carbonates, bicarbonates or alcoholates, or organic bases, for example nitrogen-containing bases, such as trialkylamines, pyridine etc.

The compounds of the formula II can be prepared by known methods (S. M. McElvain and I. D. Schroeder, J. Amer. Chem. Soc. 71, 40 (1949); and B. Harstun, DE-A No. 2 426 93). The mono-salt and the bisimidate of these compounds can be prepared from the corresponding di-salt by reacting the latter with bases, such as alkali or alkaline earth metal hydroxides, carbonates, bicarbonates or alcoholates, in an inert solvent.

The compounds of the formula III can be prepared by known methods (see, for example, Houben-Weyl, Methoden der organischen Chemie (Methods of Organic Chemistry), Volume E4, pages 522 et seq. and 580 et seq.; and DE-A No. 1 932 297 (GB-A No. 1 256 834)).

In order to avoid the interfering effects of oxygen on the reaction, it is advantageous to carry out the reaction under an inert gas atmosphere, for example under nitrogen.

The following examples are intended to illustrate the process according to the invention in greater detail:

Examples of the process

EXAMPLE 1

4,6-Dimethoxy-2-(methoxycarbonylamino)-pyrimidine 13 g (0.1 mol) of dimethyl 1,3-propanediimidate and 13.8 g (0.1 mol) of powdered, anhydrous potassium carbonate are introduced into 150 ml of tetrahydrofuran at $-10°$ C., under nitrogen blanketing. 15.6 g (0.1 mol) of methoxycarbonyl isocyanide dichloride are then added dropwise at the same temperature. The mixture is stirred for a further hour at 0° C. and then for four hours at room temperature.

The reaction mixture is worked up by being poured into water and extracted with ethyl acetate. The organic phase is washed until neutral and dried over $Na_2SO_4$. Removing the solvent by evaporation in vacuo leaves a yellowish oil, which solidifies on cooling.

Yield: 19.6 g (92% of theory)
Melting point: 92–94° C.

EXAMPLE 2

2-Acetylamino-4,6-dimethoxypyrimidine

Dimethyl 1,3-propanediimidate is reacted analogously to Example 1 with 14.0 g (0.1 mol) of acetyl isocyanide dichloride.

Yield: 17.3 g (88% of theory) of slightly yellowish crystals.
Melting point: 38–39° C.

EXAMPLE 3

2-Amino-4,6-dimethoxypyrimidine 13.0 g (0.1 mol) of dimethyl 1,3-propanediimidate and 13.8 g (0.1 mol) of pulverized, anhydrous potassium carbonate are introduced into 150 ml of (anhydrous) acetonitrile at $-20°$ C., with nitrogen blanketing. 8.9 g (0.1 mol) of dimethyl carboximidate, mixed with 20 ml of anhydrous acetonitrile, are then added dropwise at the same temperature in the course of 30 minutes. The mixture is then stirred at 0° C. for 1 hour and at room temperature for four hours.

The reaction mixture is poured into water and extracted with ethyl acetate. The organic phase is washed until neutral, dried over $Na_2SO_4$ and evaporated on a rotary evaporator.

The residue is a yellowish solid which sublimes to some extent in vacuo, giving white crystals.

Yield: 3.6 g (87.8% of theory)
Melting point 93°–94° C.

EXAMPLE 4

2-Amino-4,6-diethoxypyrimidine 15.8 g (0.1 mol) of diethyl 1,3-propanediimidate and 8.4 g (0.1 mol) of sodium bicarbonate are initially taken in anhydrous acetonitrile (150 ml) at $-10°$ C., with stirring and blanketing with nitrogen. 16.3 g (0.1 mol) of dimethyl N-acetyldithiocarboximidate, mixed with 20 ml of anhydrous acetonitrile, are then added dropwise at the same temperature. The mixture is then allowed to warm slowly up to room temperature and is stirred for a further 5 hours.

The solvent is distilled off in vacuo on a rotary evaporator and the residue (2-acetylamino-4,6-diethoxypyrimidine) is heated under reflux for 10 hours with a solution of 7.0 g (0.1 mol) of 88% strength KOH in 200 ml of methanol. The methanol is then distilled off in vacuo and the residue is taken up in water and extracted with methylene chloride. The extracts are concentrated by distillation on a rotary evaporator.

Residual crude product (2-amino-4,6-diethoxypyrimidine): 15.6 g (85% yield)
Melting point 95° C.

EXAMPLE 5

2-Ethoxycarbonylamino-4,6-dimethoxypyrimidine 10.15 g (50 mmol) of dimethyl 1,3-propanebisimidate dihydrochloride and 16.8 g (200 mmol) of $NaHCO_3$ are suspended in 100 ml of methylene chloride at $-20°$ C. and under a nitrogen atmosphere, and 20 ml of water are added.

Half the molar amount of $CO_2$ is evolved while the temperature is rising to $-5°$ C. 8.6 g (50 mmol) of ethoxycarbonyl isocyanide dichloride, mixed with 20 ml of methylene chloride, are then added dropwise at $-10$ to $-5°$ C., and the temperature is then kept at $-5$ to 0° C. for approx. 1 hour. In the course of this, the open-chain intermediate is formed; this can be detected as a polar spot in a thin layer chromatogram ($CH_2C_2/CH_3OH=95/5$). The mixture is then warmed slowly up to reflux temperature (40° C.). The second moiety of $CO_2$ is evolved. The cyclization to the desired pyrimidine derivative can be detected in a thin layer chromatogram. The mixture is kept at 40° C. for 1.5 hours and is then worked up by being partitioned in $CH_2C_2//H_2O$; the organic phase is washed again with water and, after being dried over $Na_2SO_4$, is evaporated.

The crude product is eluted with $CH_2C_2$ over a thin silica gel layer in order to remove polar impurities. The yield is 89% of theory, relative to the isocyanide dichloride employed.

EXAMPLE 6

2-Ethoxycarbonylamino-4,6-dimethoxypyrimidine 10.15 g (50 mmol) of dimethyl 1,3-propanebisimidate monohydrochloride and 12.6 g (150 mmol) of $NaHCO_3$ are suspended in 100 ml of methyl isobutyl ketone (MIBK) at $-20°$ C. and under a nitrogen atmosphere, and 20 ml of water are added. $CO_2$ is evolved while the temperature is rising to $-5°$ C. 8.6 g (50 mmol) of ethoxycarbonyl isocyanide dichloride, mixed with 20 ml of MIBK, are then added dropwise at $-5°$ C., and the temperature is then kept at $-5$ to 0° C. for approx. 1 hour. The open-chain intermediate is formed in the course of this; it can be detected as a polar spot in a thin layer chromatogram ($CH_2Cl_2/CH_3H=95/5$). The mixture is then warmed slowly up to reflux temperature (40° C.). $CO_2$ is evolved once more. The cyclization to give the desired pyrimidine derivative can be detected in the thin layer chromatogram. The mixture is left for 1.5 hours at 40° C. and is then worked up by being partitioned in $MIBK/H_2O$; the organic phase is washed again with water and, after being dried over $Na_2SO_4$, is evaporated. The crude product is eluted with $CH_2Cl_2$ over a thin silica gel layer in order to remove polar impurities. The yield is 88% of theory, relative to the isocyanide dichloride employed.

Further compounds of the formula I having the meanings of $R^1$, $R^2$, $R^3$, X and Y defined in the following table can be prepared analogously to the procedures described in Examples 1–6 by reacting compounds of the formula II in which $R^1$, $R^2$, X and Y have the meanings mentioned in the table, with compounds of the formula III in which $R^3$ and $R^5$ have the meanings defined in the table:

| Example | $R^1$ | $R^2$ | X | Y | $R^3$ | $R^5$ |
|---|---|---|---|---|---|---|
| 7 | $C_2H_5$ | $C_2H_5$ | O | O | $COCH_3$ | Cl |
| 8 | $C_2H_5$ | $C_2H_5$ | O | O | $COCH_3$ | Cl |
| 9 | $CH_3$ | $CH_3$ | O | O | $COOC_6H_5$ | Cl |
| 10 | $C_2H_5$ | $C_2H_5$ | O | O | $COOC_6H_5$ | Cl |
| 11 | $CH_3$ | $CH_3$ | O | O | $COCH_2Cl$ | $SC_2H_5$ |
| 12 | $CH_3$ | $CH_3$ | O | O | $COCHCl_2$ | Cl |
| 13 | $CH_3$ | $CH_3$ | O | O | $COCCl_3$ | Cl |
| 14 | $C_2H_5$ | $C_2H_5$ | S | S | $COOCH_3$ | $OC_2H_5$ |
| 15 | $CH(CH_3)_2$ | $CH(CH_3)_2$ | O | O | $COOCH_3$ | Cl |
| 16 | $CH_3$ | $CH_3$ | O | S | $COOCH_3$ | Cl |
| 17 | $C_2H_5$ | $C_2H_5$ | O | S | $COOCH_3$ | Cl |
| 18 | $CH_3$ | $CH_3$ | O | S | $COC_2H_5$ | $SCH_3$ |
| 19 | $C_2H_5$ | $C_2H_5$ | O | O | $COOC_2H_5$ | Cl |
| 20 | $CH_2Cl$ | $CH_2Cl$ | O | O | $COOCH_3$ | Cl |
| 21 | $CH_2Cl$ | $CH_2Cl$ | O | O | $COC_2H_5$ | Cl |
| 22 | $CH_2Cl$ | $CH_2Cl$ | O | O | $COOC_6H_5$ | Cl |
| 23 | $CH_2Cl$ | $CH_2Cl$ | S | S | $COOCH_2Cl$ | $SC_6H_5$ |
| 24 | $CF_3$ | $CF_3$ | O | O | $COOCH_3$ | $SC_6H_5$ |
| 25 | $CF_3$ | $CF_3$ | O | O | $COOC_2H_5$ | $OC_6H_5$ |
| 26 | $CF_3$ | $CF_3$ | S | S | $COOC_2H_5$ | Cl |
| 27 | $CH_2OCH_3$ | $CH_2OCH_3$ | O | O | $COOCH_3$ | Cl |
| 28 | $CH_2OC_2H_5$ | $CH_2OC_2H_5$ | O | S | $COOCH_3$ | Cl |
| 29 | $CH_2OC_2H_5$ | $CH_2OCH_3$ | O | O | $COOC_2H_5$ | Cl |

We claim:

1. A process for the preparation of a compound of the formula I

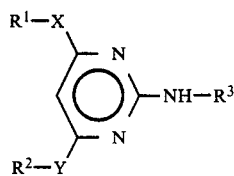

in which

X and Y independently of one another are oxygen or sulfur and $R^1$ and $R^2$ independently of one another are $(C_1-C_4)$alkyl, $(C_1-C_4)$alkoxy-$(C_1-C_2)$alkyl or halogeno-$(C_1-C_4)$alkyl and $R^3$ is H or a radical $-COR^4$ in which $R^4$ is $(C_1-C_4)$alkyl, halogeno-$(C_1-C_4)$alkyl, $(C_1-C_4)$alkoxy, halogeno$(C_1-C_4)$alkoxy, phenyl or phenoxy, the latter both of which are unsubstituted or monosubstituted to trisubstituted by halogen, $(C_1-C_4)$alkoxy or $(C_1-C_4)$alkyl, which comprises reacting a propanediimidate of the formula II

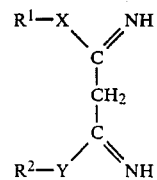

in which $R^1$ and $R^2$ are as defined in formula I, or one of its salts, in an inert solvent and in the presence of a base, with a carbonic acid imine derivative of the formula III

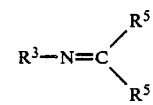

in which $R^3$ is as defined in formula I and the $R^5$s independently of one another are halogen, $(C_1-C_4)$alkoxy, $(C_1-C_4)$alkylthio, phenoxy or phenylthio, to provide a compound of the formula I.

2. The process as claimed in claim 1, wherein X and Y denote oxygen and $R^1$ and $R^2$ independently of one another denote $(C_1-C_4)$alkyl.

3. The process as claimed in claim 1, wherein $R^3$ denotes a hydrogen atom or a $-COR^{14}$ radical in which $R^{14}$ denotes $(C_1-C_4)$alkyl or $(C_1-C_4)$alkoxy and each of the $R^{15}$s denotes $(C_1-C_4)$alkoxy or $(C_1-C_4)$alkylthio.

4. The process as claimed in claim 1, wherein $R^3$ denotes a radical of the formula $-COR^{14}$ in which $R^{14}$ denotes $(C_1-C_4)$alkyl or $(C_1-C_4)$alkoxy, and each of the $R^{15}$s denotes chlorine.

5. The process as claimed in claim 1, wherein the bases employed are alkali or alkaline earth metal hydroxides, carbonates, bicarbonates or alcoholates, trialkylamines, pyridine or the compound of the formula II itself.

6. The process as claimed in claim 1, wherein the inert solvent used is a solvent selected from to the group consisting of containing aliphatic alcohols having 1 to 4 carbon atoms, aliphatic ketones, aliphatic and cycloaliphatic ethers, halogenated aliphatic hydrocarbons having 1 to 3 carbon atoms, aliphatic esters having a total of 3 to 6 carbon atoms, aliphatic hydrocarbons having 5 to 2 carbon atoms, aromatic and cycloaliphatic hydrocarbons having 5 or 6 ring atoms, aliphatic nitriles having 1 to 4 carbon atoms, and mixtures of at least 2 of the solvents mentioned.

7. The process as claimed in claim 6, wherein the inert solvent used is a solvent selected from the group consisting of methanol, ethanol, acetone, methyl isobutyl ketone, diethyl ether, dioxane, tetrahydrofuran, methylene chloride, chloroform, alkyl acetates having 1 to 4 carbon atoms in the alkyl radical, hexane, toluene, xylenes, cyclohexane and acetonitrile.

8. The process as claimed in claim 1, wherein the reaction is carried out at a temperature from $-20°$ to $100°$ C.

9. The process as claimed in claim 8, wherein the reaction is carried out at $-20°$ to $60°$ C.

10. The process as claimed in claim 1, wherein the process is carried out under an inert gas atmosphere.

* * * * *